US005728874A

United States Patent [19]

Mullins et al.

[11] Patent Number: 5,728,874
[45] Date of Patent: Mar. 17, 1998

[54] ANTI-HIV ACHIRAL POLYUREA OLIGOMERS, A PROCESS FOR CREATING THEM, FORMULATIONS USING THEM, AND THEIR USE IN THE TREATMENT OF AIDS

[75] Inventors: Michael J. Mullins; Ray E. Drumright, both of Midland, Mich.; Alan D. Cardin; Norton P. Peet, both of Cincinnati, Ohio

[73] Assignees: Merrell Pharmaceuticals, Inc., Cincinnati, Ohio; The Dow Chemical Co., Midland, Mich.

[21] Appl. No.: 174,597

[22] Filed: Dec. 27, 1993

Related U.S. Application Data

[63] Continuation-in-part of Ser. No. 710,370, Jun. 10, 1991, Pat. No. 5,276,182, which is a continuation-in-part of Ser. No. 549,782, Jul. 9, 1990, abandoned.

[51] Int. Cl.$^6$ ............................ C07C 273/00; C61K 31/17
[52] U.S. Cl. .................................. 564/49; 564/50; 564/51; 564/52; 564/53; 574/588; 574/595
[58] Field of Search ...................... 564/49–53; 514/588, 514/595, 596

[56] References Cited

U.S. PATENT DOCUMENTS

| 2,833,744 | 5/1958 | Neher | 260/77.5 |
|---|---|---|---|
| 3,528,949 | 9/1970 | Rutledge | 260/77.5 |
| 4,104,262 | 8/1978 | Schade | 528/295 |
| 4,107,202 | 8/1978 | Conrow et al. | 260/506 |
| 4,328,244 | 5/1982 | Daniel et al. | 424/304 |
| 4,349,568 | 9/1982 | Markley et al. | 424/330 |
| 4,471,110 | 9/1984 | Christell | 528/337 |
| 4,604,404 | 8/1986 | Munson et al. | 514/494 |
| 4,736,014 | 4/1988 | Engelhardt et al. | 528/295 |
| 4,783,446 | 11/1988 | Neushul | 514/54 |
| 4,824,916 | 4/1989 | Kershner et al. | 525/420 |
| 4,895,660 | 1/1990 | Kershner et al. | |
| 4,966,894 | 10/1990 | Herr et al. | 514/56 |
| 5,276,182 | 1/1994 | Cardin et al. | 564/49 |
| 5,424,063 | 6/1995 | Cardin et al. | 424/78.08 |

FOREIGN PATENT DOCUMENTS

| 0498095 | 2/1991 | European Pat. Off. |
| 2105446 | 4/1972 | France . |
| 2307832 | 4/1976 | France . |
| 2669535 | 5/1992 | France . |
| 3345902 | 12/1983 | Germany . |
| 0147822 | 11/1981 | Japan . |
| 90/0094 | 10/1990 | South Africa . |
| 781479 | 8/1957 | United Kingdom . |
| 0907829 | 10/1962 | United Kingdom . |
| 1393557 | 5/1975 | United Kingdom . |
| 8800828 | 2/1988 | WIPO . |
| 9200749 | 1/1992 | WIPO . |

OTHER PUBLICATIONS

*Amer. Chem. Soc. Symp. Ser,* "Biological Activities of Polymers" No. 182, pp. 205–220, (1982).
*Principles of Polymerization,* 2d, pp. 20–25, G. Odian (1981).
*Protein Purification,* pp. 186–198 (1987) R. K. Scopes.
*Polymer Fractionation,* pp. 43–65, (1967) A. KoterA.
*Polymer Fractionation,* p. 462, (1967).
*J. Chrom. Library,* 41A, pp. A127–A208, A303–A399. (1985).
*Protein Purification,* pp. 199–215, (1987) R. K. Scopes.
*Dowex: Ion Exchange,* the Dow Chemical Company, (1958), pp. 39–66.
*Macromolecules,* V. 1, Ch. 8, (1984).
P.M. Rosoff et al., J. Med. Chem 263(36), 19535–19540 (1973).
C&E News, p. 11 (Jul. 16, 1990).
Chem. Abstracts, polyamides vol. 102, No. 62707 (1985), Toshiba Corp., Japan, "Block Copolymers" JP 59179521 A2 841012.
Antiviral Research, 18(1992), Sulfonic acid polymers as a new class of human immunodefic–ciency virus inhibitors, Prem Mohan, et al., pp. 139–150.
Komp et al, Chemical Abstracts vol. 110 Abstract No. 33727k (1989).
Hofferek et al., Chemical Abstracts vol. 114: 180333q (1990).
Berge et al., J Pharm. Sciences 66(1), pp. 1–19, 1977.
Vandenberg E.J. et al., *Polymeric Materials Science and Engineering,* vol. 57, Fall Meeting 1987, pp. 139–143.

*Primary Examiner*—C. H. Kelly
*Attorney, Agent, or Firm*—Stephen L. Nesbitt

[57] ABSTRACT

The present invention relates to achiral polyurea oligomers, their uses and formulations as anti-HIV pharmaceuticals and to a process for the preparation of narrow mono- and polydispersed oligomers as an emodiment of the invention. The achiral oligomers are derived from repeating units of the monomer 4,4'-diamino-biphenyl-3,3'-disulfonic acid and are water soluble, have a rigid backbone, possess ordered anionic spacing and have a number average molecular weight of <20,000. The process relates to the synthesis of narrow poly- and mono-dipersed oligomers comprising the steps of: 1) restricting the crude olydispersed anionic oligomer mixture to a narrow polydispersed anionic oligomer mixture to a narrow polydispersed anionic oligomer mixture; and/or 2) isolating the monodispersed anionic oligomer; and 3) optionally converting the narrow poly- or mono-dispersed anionic oligomer salt from Step 1 or 2 to a desired pharmaceutically-acceptable salt, especially a solim or potassium salt. The process steps may be executed whereby step 1 or 2 is done alone, each in combination with Step 3, or all three steps are done.

50 Claims, No Drawings

ANTI-HIV ACHIRAL POLYUREA OLIGOMERS, A PROCESS FOR CREATING THEM, FORMULATIONS USING THEM, AND THEIR USE IN THE TREATMENT OF AIDS

CROSS-REFERENCE TO RELATED APPLICATIONS

This is a continuation-in-part of Ser. No. 710,370, filed Jun. 10, 1991, now U.S. Pat. No. 5,276,182, which is a continuation-in-part of Ser. No. 549,782, filed Jul. 9, 1990, now abandoned. Other related applications are: Ser. No. 965,248, filed Jan. 7, 1993, which is a continuation-in-part of Ser. No. 549,782, filed Jul. 9, 1990, now abandoned; and Ser. No. 132,551, filed Oct. 6, 1993, which is a divisional of Ser. No. 549,782, filed Jul. 9, 1990, now abandoned.

FIELD OF THE INVENTION

This invention concerns achiral polyurea oligomers, their uses and formulations, as well as processes for their preparation. The present oligomers are anionic compounds that have particularly valuable anti-human immunodeficiency virus activity and these oligomers are thus useful in the treatment of acquired immune deficiency syndrome (AIDS).

BACKGROUND OF THE INVENTION

A great deal of research is currently underway to develop treatments and cures for viral infections in humans and in animals. Notably the incidence of AIDS and AIDS related complex (ARC) in humans is increasing at an alarming rate. The five year survival rate for those with AIDS is dispiriting and AIDS patients, whose immune systems have been seriously impaired by the infection, suffer from numerous opportunistic infections including *Kaposi's sarcoma* and *Pneumocystis carinii pneumonia*. No cure for AIDS is known and current treatments are largely without adequate proof of efficacy and have numerous untoward side effects. Fear of the disease has resulted in social ostracism of and discrimination against those having or suspected of having the disease.

It has been disclosed in South African Patent 90/0094, issued Oct. 31, 1990, that a purified form of heparin, a sulfated polysaccharide, binds through interactions to a viral protein which is responsible for cell recognition and provides limited inhibition of host cell infection. However, heparin causes some side effects, notably hemorrhage and increased clot formation time as well as thrombocytopenia. Use of heparin is contraindicated in patients who are actively bleeding, or have hemophilia, purpura, thrombocytopenia, intracranial hemorrhage, bacterial endocarditis, active tuberculosis, increased capillary permeability, ulcerative lesions of the gastrointestinal tract, severe hypertension, threatened abortion or visceral carcinoma. The contraindication for use by hemophiliacs is particularly of concern because many such individuals are now HIV positive.

It has long been recognized that certain synthetic, water-soluble polymers exhibit a broad spectrum of biological activity [R. M. Ottenbrite in "Biological Activities of Polymers", *Amer. Chem. Soc. Symp. Ser.*, No. 182, pp. 205–220, eds. C. E. Carraher and C. G. Gebelein (1982)]. Although the mechanism of action of such water-soluble polymers is unknown, one postulate is that the polymer binds to the viral membrane, through an ionic attraction, thus rendering the virus unable to infect host cells. Unfortunately, the extreme toxicity of these polymers has prevented their clinical use. Also, these polymers have a high molecular weight and are unable to pass through the renal membranes.

Attempts have been made to circumvent the toxicity and excretion problems by synthesis of low molecular weight (1,000 to 10,000) aliphatic polymers [R. M. Ottenbrite in "Biological Activities of Polymers", *Amer. Chem. Soc. Symp. Ser.*, No. 182, pp. 205–220, eds. C. E. Carraher and C. G. Gebelein (1982)]. It has been found that such polymers are less toxic but have much reduced anti-viral activity. These low molecular weight aliphatic polymers may be classed as "random coil" polymers. Such polymers have an unpredictable configuration because of the flexibility of the backbone linking groups. The configuration of random coil polymers in solution may be generally described as globular. The reduced anti-viral activity of these random-coil polymers is believed to be due to a low binding affinity of the polymers with the viral membrane.

One approach to overcome the problems with the random-coil polymers would be to provide polymers which have rigid backbones with few degrees of freedom, and have a defined solution configuration.

Certain anionic oligomers which inhibit viral replication without the side effects shown by heparin and known polymers have now been found. These anionic oligomers have ordered anionic spacing, have a rigid backbone, and are water-soluble. The anionic oligomers, as polydispersed mixtures, have been described in our copending U.S. patent application Ser. No. 710,370, filed Jun., 10, 1991, and corresponding PCT application Ser. No. PCT/US91/04804, filed Jul. 8, 1991, the disclosures of which are hereby incorporated by reference. The anionic oligomers, as narrow poly- and mono-dispersed oligomers, have been described in U.S. patent application Ser. No. 818,753, filed Jan. 9, 1992, the disclosure of which is hereby incorporated by reference. The oligomers described in the above-identified applications are chiral due to the presence of a chiral biphenyl unit in the monomer molecule and are, therefore, mixtures of enantiomers (mirror-image forms).

The chiral drugs that exist as two or more enantiomers are frequently offered by drug companies as racemates. There are a number of emerging issues associated with the use of racemates as drugs. Some of the issues include: undesirable side effects possibly associated with the inactive enantiomer in the racemate mixture, concern over the excess dosage of the racemate taken if only one enantiomer is active, and the likelihood that the two enantiomers in the racemate may have different pharmacological actions and could be advantageously exploited individually. There is, consequently, a growing concern and increasing uncertainty in the drug industry as to the FDA's position with regard to the extent of the justification that would be required for the FDA approval of the racemates, and whether the drug companies will be required to develop chiral drugs as single enantiomers. Many drug companies are either expending (or weighing whether to expend) efforts towards synthesis of only pure enantiomers of chiral drugs, avoidance of asymmetric molecules entirely, or the resolution of racemates into enantiomers.

Clearly, it would be desirable to develop polymers which have rigid backbones with few degrees of freedom and are achiral. It would be further desirable that the polymers have a narrow molecular weight range, low toxicity, and be easily characterized.

SUMMARY OF THE INVENTION

It has been found that polyurea oligomers comprising recurring moieties derived from the diamine compound corresponding to Formula (I)

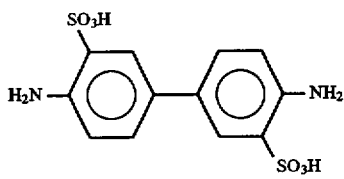

are achiral. The diamine of Formula (I) has bulky sulfonate groups in the positions meta to the biphenyl linkage. The sulfonate groups do not restrict rotation about the biphenyl bond and as a consequence, the biphenyl is achiral.

In contrast, the ortho substituted diamine disclosed in our pending applications (Ser. Nos. 710,370, and 818,753) and represented by Formula (II)

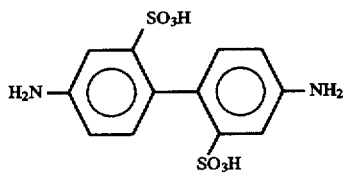

is chiral due to hindered rotation about the biphenyl bond caused by the presence of sulfonate groups in the ortho position with respect to the biphenyl bond.

In one aspect, therefore, the present invention relates to water-soluble, rigid backbone, achiral polyurea oligomer comprising recurring moieties derived from

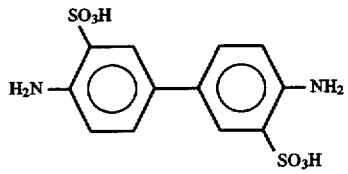

The oligomers of the invention possess ordered anionic spacing between the anionic sulfonic acid groups. The number average molecular weight $M_n$ of the oligomers is less than 20,000.

In another aspect, the present invention relates to a process for preparing the narrow poly- and mono-dispersed anionic achiral polyurea oligomers of the invention, comprising the steps of:

1) restricting the crude polydispersed anionic oligomer mixture to a narrow polydispersed anionic oligomer mixture; and/or
2) isolating the monodispersed anionic oligomer; and
3) optionally converting the narrow poly- or mono-dispersed anionic oligomer salt from Step 1 or 2 to a desired pharmaceutically-acceptable salt, especially a sodium or potassium salt.

In the above process, the following combination of steps are intended: Step 1 or 2 is done alone; Step 1 or 2 is followed by step 3; or all three steps are done.

The achiral polyurea oligomers of the invention are useful as anti-human immunodeficiency virus activity agents and are thus useful in the treatment of AIDS, and ARC. The oligomers include their pharmaceutically-acceptable salts.

DETAILED DESCRIPTION OF THE INVENTION

The oligomers of the invention are represented by the Formula:

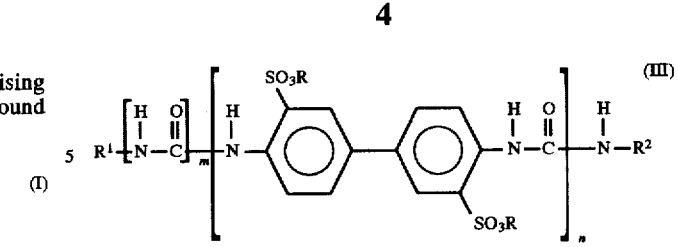

wherein:

$R^1$ is a hydrogen, $C_1$–$C_4$ alkyl group, phenyl, or a phenyl substituted with 0 or 2 $SO_3R$ groups and up to 3 substituents independently selected from a chloro or a bromo atom, or a $C_1$–$C_{20}$ alkyl group;

R is a hydrogen atom or a pharmaceutically-acceptable cation;

$R^2$ is —$R^1$ or —X—$NHR^1$, where in $R^1$ is as defined above; X is:

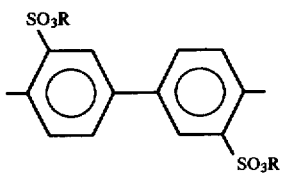

m is an integer 0 or 1, with the proviso that when m is 0, $R^1$ is a hydrogen atom, and n is an integer from 3 to 50.

Preferred terms for Formula I are as follows:

$R^1$ and $R^2$ are a 4-methylphenyl group;

m is 1; and n is 3 to 15.

The term "pharmaceutically-acceptable cation" means a cation acceptable for pharmaceutical use. Those cations that are not substantially toxic at the dosage administered to achieve the desired effect and do not independently possess significant pharmacological activity are included within the term "pharmaceutically-acceptable cation". Illustratively, these salts include those of alkali metals, such as sodium and potassium; alkaline earth metals, such as calcium and magnesium; ammonium; light metals of Group IIIA, including aluminum; and organic primary, secondary and tertiary amines, such as trialkylamines, including triethylamine, procaine, dibenzylamine, N,N'-dibenzylethylenediamine, dihydroabietylamine, N-($C_1$–$C_4$)alkylpiperidine, and any other suitable amine. Sodium and potassium salts are preferred.

The term "pharmaceutically-acceptable" means suitable for administration to warm-blooded animals, especially human beings, and includes being nontoxic, e.g. suitable for pharmaceutical use and is not poisonous to the warm-blooded animal. The pharmaceutically-acceptable cations of the oligomers of the present invention are prepared by conventional ion exchange processes or by treating the $R^1$ acid with an appropriate base.

When uses other than for pharmaceuticals are the object for the present oligomers, then salts that would otherwise not be as acceptable for pharmaceutical uses may be employed. Examples of such additional salts include barium, zinc and titanium.

By "ordered anion spacing" or "regular spacing between anionic groups" is meant that the anionic sulfonic acid groups are present in the backbone of the polymer at intervals determined by the starting material reagent used and the occurrence of the anionic groups is controlled in a predictable manner. While not wishing to be bound by any theory, the sulfonic acid groups of the oligomers are believed to be the portion that binds to the HIV and/or cell membrane and thereby interrupts the ability of the virus to replicate.

The terms "monodispersed" and "polydispersed" oligomers (and similar terms) refer to the distribution of oligomers in the sample. The polydispersity in a sample is measured by the ratio of the weight average molecular weight, $M_w$, to the number average molecular weight, $M_n$. (See G. Odian, "Principles of Polymerization", 2d ed., pp. 20–25, John Wiley & Sons, 1981.) For the purposes of this invention, "crude polydispersed" oligomer samples are $M_w/M_n => 1.3$. For the purposes of this invention, an oligomer is a "narrow polydispersed" oligomer when $M_w/M_n = 1.0$ to 1.3; preferably from 1.0 to 1.2; and more preferably from 1.0 to 1.15. The narrow polydispersed oligomer has been prepared from the crude polydispersed oligomer mixture. For the purposes of this invention, an oligomer is a "monodispersed" oligomer when $M_w/M_n = 1.0$ to 1.1, which is a narrower range within the narrow polydispersed range. The term "narrow molecular weight range" refers to the decrease of the polydispersity ratio by some amount compared to the prior sample.

The purity of each monodispersed fraction of any desired n fraction is at least 75 percent, preferably from about 85 to about 100 percent. Purity is defined as the area ratio of the desired oligomer relative to the area of all peaks observed on an analysis by liquid chromatography.

As used herein, the term "oligomer" encompasses all the possible values for n, e.g., 3 through 50. The oligomers are preferably linear with n equal to an integer from 3 to 50, preferably from 3 to 20, more preferably from 3 to 15. Of course, the n value is directly related to the molecular weight of the resulting oligomer. It is essential that these oligomers are of sufficiently low molecular weight in order to pass through the renal excretory membrane, but also able to inhibit the HIV virus. The average molecular weight is governed by the stoichiometry of the reagents. The number average molecular weight ($M_n$) is <20,000, preferably from about 1,000 to about 8,000, and most preferably from about 1,000 to about 6,000.

For the purpose of the present invention, the oligomers described herein and physiologically-acceptable salts thereof are considered equivalent. Physiologically-acceptable salts refer to the salts of those bases which will form a salt with at least one acid group of a sulfonic acid group and which will not cause significant adverse physiological effects when administered as described herein. Suitable bases include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like; and ammonia, primary, secondary and tertiary amines and the like. Particularly preferred bases are the alkali metal hydroxides, carbonates, and bicarbonates. Physiologically-acceptable salts may be prepared by conventional ion exchange processes or by treating the $R^1$ acid with an appropriate base. Examples of additional salts have been described herein.

The formulations of the present invention are in the solid or liquid form. These formulations may be in kit form such that the components are mixed at the appropriate time prior to use. Whether premixed or as a kit, the formulations usually require a pharmaceutically-acceptable carrier or adjuvant.

The oligomers of the present invention are soluble in water and in salt solutions, especially at physiological pH and in saline solutions. Thus the present oligomers are readily formulated into a suitable aqueous pharmaceutical dosage form. Also, after the present oligomer formulation is administered, the oligomer remains soluble in vivo.

The present invention also concerns a process for the preparation of narrow poly- and mono-dispersed achiral anionic oligomers that have a narrow molecular weight range which enables these oligomers to be used as pharmaceutical agents in a substantially pure enantiomeric form, particularly in humans, for the treatment of AIDS or ARC. The resulting advantages of having a narrow molecular weight range for these achiral oligomers are greater activity than the corresponding mixtures, better characterization of the oligomers, and ease of analysis of the biological activity of the achiral oligomer.

The present invention is directed to a process for the isolation of the above oligomers into their individual components, e.g., monodispersed oligomers and to the isolated oligomer product so prepared.

In the process to prepare the narrow poly- and mono-dispersed anionic achiral oligomers of the present invention, the various steps may be performed in the following manner.

Step 1—restricting the crude polydispersed anionic oligomer mixture to a narrow polydispersed anionic oligomer mixture—may be accomplished by gel filtration, selective precipitation, membrane permeation, or reverse phase chromatography; and/or Step 2—isolating the monodispersed anionic oligomer—may be accomplished by gel electrophoresis or reverse phase chromatography. The monodispersed purity of each desired n fraction is at least 75 percent, preferably from about 85 to about 100 percent; and Step 3—optionally converting the narrow poly- or monodispersed anionic oligomer salt from Step 1 or 2 to a desired pharmaceutically-acceptable salt, especially the sodium or potassium salt—may be accomplished by either ion exchange, particularly when the tetrabutyl ammonium salt has been formed, or by the addition of a salt of a weak, volatile acid.

In the process of the present invention, the methods employed are those customary and known in the art. As these techniques are known, some examples of a description of these methods can be found as follows:

Gel filtration—*Protein Purification*, ed. Charles R. Cantor, Springer-Verlag, 1987, in the chapter by Robert K. Scopes, "Separation in Solution", pp. 186–198.

Selective precipitation—*Polymer Fractionation*, ed. Manfred J. R. Cantow, Academic Press, 1967, in the chapter by Akira Kotera, "Fractional Precipitation", pp. 43–65.

Membrane permeation—*Polymer Fractionation*, ed. Manfred J. R. Cantow, Academic Press, 1967, pp. 462.

Reverse phase chromatography—*J. Chrom. Library*, 41A, "High-Performance Liquid Chromatography of Biopolymers and Biooligomers", ed. O. Mikes, Elsevier, 1988, pp. A127–A208, A303–A399.

Gel electrophoresis—*Protein Purification*, ed. Charles R. Cantor, Springer-Verlag, 1987, in the chapter by Robert K. Scopes, "Separation in Solution", PP. 199–215.

Ion exchange—Dowex: *Ion Exchange*, The Dow Chemical Company, The Lakeside Press, 1958, pp. 39–66.

Addition of a salt of a weak, volatile acid—oligomers in solution as ammonium salts of volatile amines can be converted to more preferred pharmaceutically-acceptable salts, such as the sodium or potassium salts, by treating the solution with an alkali metal salt of a weak volatile acid. Upon concentrating the solution by evaporation or lypholization, the amine and weak acid are removed and the oligomers are isolated as their alkali metal salts. Suitable examples of ammonium salts which may be converted in the step are salts of ammonia, monoethylamine, triethylamine, trimethylamine or dimethylamine (herein referred to as "ammonium salts"). Examples of alkali metal salts are sodium or potassium hydroxide, bicarbonate, acetate, formate or propionate.

Preparation of the Crude Polydispersed Anionic Oligomer Starting Materials.

The crude polydispersed anionic oligomers used as starting materials in the process of the present invention to prepare the narrow poly- and mono-dispersed achiral anionic oligomers of the present invention are prepared by the process described in our copending U.S. patent application Ser. No. 710,370, filed Jun. 10, 1991, the disclosure of which is hereby incorporated by reference. The process to prepare these polydispersed oligomers uses a modification of the procedure of Kershner (U.S. Pat. No. 4,895,660, the disclosure of which is hereby incorporated by reference, and described further below) by replacing a portion of one of the difunctional monomers with a mono-functional end-capping agent and running the reaction in the absence of a surfactant. The number average molecular weight ($M_n$) is governed by the stoichiometry of the reactants.

The process for the preparation of the polyureas is further explained as follows.

Diamines: The diamine of the present invention is represented by Formula (I) above.

It has been discovered that the diamine can be prepared by reacting 2-nitrobenzene sulfonyl chloride (commercially available from Aldrich) with aqueous sodium hydroxide in the presence of zinc. A specific Example illustrating the preparation of the diamine is set forth in the Examples herein below.

The achiral characteristic of the diamine compound, 4,4'diaminobiphenyl-3,3'-disulfonic acid, represented by Formula (I) can be determined by the methods known in the art. One method includes reacting the diamine with a chiral reactant, and analyzing the product by nuclear magnetic resonance (NMR) spectroscopy. A simple NMR spectrum of the product indicates an absence of diastereoisomers and the achiral nature of the diamine of Formula (I).

In contrast, the reaction of the chiral diamine, 4,4'-diaminobiphenyl-2,2'-disulfonic acid, represented by Formula (II), with a chiral reactant results in a product which is a mixture of two diastereomers giving two sets of NMR signals. A specific example to illustrate the achiral nature of the diamine compound of Formula (I) is described in the Examples hereinbelow.

Difunctional electrophiles: Phosgene (carbonyl dichloride) and carbonyl dibromide, and other urea precursors such as carbonyl diimidazole, hexachloroacetone, $Cl_3COCO_2CCl_3$, $CCl_3COCl$, and $Cl_3OCOCl$ may be used.

Acid Acceptors: A variety of inorganic bases may be used, such as alkali metal or divalent metal hydroxides carbonates, bicarbonates, phosphates. Acid acceptors with buffering capacity are preferred when all of the base is added prior to the addition of the difunctional electrophile. Organic bases such as trialkyl amines may be used, but are not preferred.

Monofunctional end capping agent: A variety of such molecular weight limiting agents may be used. Such agents may be aliphatic or aromatic compounds which react with the diamines or the difunctional electrophiles. Examples of suitable monofunctional agents are amines such as aniline, methylaniline, substituted anilines, for example p-toluidine, methylamine, ethylamine, butylamine, diethylamine, ammonia N-methylaniline, phenol and cresol. Examples of monofunctional amine reactive agents are benzoyl chloride, methyl benzoyl chloride, acetyl chloride, and phenyl chloroformate. These end-capping agents may also contain charged substituents, for example 2-hydroxybenzene sulfonic acid potassium salt or 4-aminobenzenesulfonic acid potassium salt.

Miscellaneous additives: The addition of surfactants is not necessary or preferred, and can complicate the isolation process.

Solvents: A single solvent, water, is preferred when the difunctional electrophile is a liquid at the reaction temperature. An example of such a difunctional electrophile is phosgene. When solid, water insoluble reactants are used, a small amount of a water immiscible cosolvent is desirable. Example of such water immiscible cosolvents are chloroform, carbon tetrachloride, toluene, and methylene chloride. Typical ratios of organic to aqueous solvents are 0:1, with 0:0.1 preferred.

The process is conducted at temperatures which allow the reaction to proceed, typically from about 0° to 100° C. Preferable temperatures are 0° to 25° C. When low boiling starting materials are used, for example phosgene (bp 6° C.), it is advantageous to operate at temperatures at or below the boiling point. The pressure is not important and typically ambient pressure is employed. The pH of the reaction must be carefully maintained for optimum process. At low pH (<6) the reaction is very slow, while at high pH (>10) the difunctional electrophile is susceptible to attack by hydroxide or other base. Degradation of the polyurea can also occur at high pH. The pH is preferably maintained between 7 and 9.

When no end-capping agent is used, molecular weight control can be achieved by careful adjustment of the stoichiometry of the reactants. Either the diamine or the difunctional electrophile may be used in excess, for example from 1 to 100 percent molar excess. This stoichiometry must account for any of the difunctional electrophile which is destroyed by hydrolysis prior to reaction with the diamine. For example, when phosgene is used at high pH, a large excess is required to compensate for the fast reaction with hydroxide which destroys it. Because the extent of this side reaction is difficult to control, a monofunctional end capping agent is preferably used to control the molecular weight. Although the techniques mentioned can be used to control the number average molecular weight, the products are mixtures of polymers with several molecular weights characterized by a distribution.

The order of addition of the reactants is not critical. However, the preferred order is to add the difunctional electrophile first. When acid acceptors which are not buffers are used, such as hydroxide, it is most preferable to add a portion at the beginning to achieve the desired pH, and then add the remainder concurrently with the difunctional electrophile.

Finally, it is desirable to conduct these polymerizations at high concentrations. This reduces the amount of solvent which must be removed to isolate the product. Also, in certain cases the product precipitates from the reaction solution near the end of the reaction, and may be isolated by simply decanting the solvent. Most of the inorganic salt which results from reaction of the acid acceptor is removed in this process. The concentration is not critical, and may be from 0.5 to 50 weight percent, expressed as weight of diamine to weight of solvent. A preferred range is 0.5 to 5 weight percent.

The crude polydispersed product may be isolated by precipitation of the reaction solution into a solvent which is water miscible but is a poor solvent for the product. Examples of such solvents are acetone, methanol, ethanol, isopropanol.

Method of use

Anti-HIV achiral anionic oligomers can be used to prevent syncytium formation in cells infected with HIV-I virus or other related viruses having gp120 surface protein. Anti-HIV anionic oligomers can be used to treat AIDS and ARC and other diseases caused by the retrovirus HIV-I or other related viruses having gp120 surface protein. The narrow poly- and mono-dispersed achiral anionic oligomers of this invention can be used as a pure compound, or as mixtures, such as those of a range of n values, or as mixtures with other known agents for the present anti-viral utilities.

The amount of anti-HIV achiral anionic oligomers which is needed to prevent syncytium formation in HIV infected cells can be any effective amount. Experimentally, it has been determined that anti-HIV anionic oligomers, when employed at a concentration of 10 µg/mL of aqueous formulation, resulted in complete inhibition of syncytium formation as well as a reduction in the presence of p24 antigen, an indicator of viral replication, to below 300 pg/mL. The amount of anti-HIV achiral anionic oligomers to be administered in order to treat AIDS or ARC or other disease caused by HIV infection can vary widely according to the particular dosage unit employed, the period of treatment, the age and sex of the patient treated, the nature and extent of the disorder treated, and other factors well-known to those practicing the medical arts. Moreover anti-HIV oligomers can be used in conjunction with other agents known to be useful in the treatment of retroviral diseases and agents known to be useful to treat the symptoms of and complications associated with diseases and conditions caused by retroviruses.

The anti-HIV effective amount of anti-HIV achiral anionic oligomers to be administered according to the present invention will generally range from about 0.1 mg/kg to about 500 mg/kg of body weight of the patient and can be administered one or more times per day. Anti-HIV achiral anionic oligomers can be administered with a pharmaceutical carrier using conventional dosage unit forms either orally or parenterally.

For oral administration, anti-HIV achiral anionic oligomers can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, sorbitol, calcium phosphate, and cornstarch. In another embodiment the achiral anionic oligomers of this invention can be tableted with conventional tablet bases such as lactose, sucrose, and cornstarch in combination with binders such as acacia, cornstarch, or gelatin; disintegrating agents intended to assist the break-up and dissolution of the tablet following administration such as potato starch, alginic acid, corn starch, and guar gum; lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents; and flavoring agents intended to enhance the aesthetic qualities of the tablets and make them more acceptable to the patient.

Suitable excipients for use in oral liquid dosage forms include diluents such as water and alcohols, for example, ethanol, benzyl alcohol, and the polyethylene glycols, either with or without the addition of a pharmaceutically-acceptable surfactant, suspending agent, or emulsifying agent.

The anti-HIV achiral anionic oligomers of this invention may also be administered parenterally, that is, subcutaneously, intravenously, intramuscularly, or interperitoneally, as injectable dosages of the anionic oligomers in a physiologically acceptable diluent with a pharmaceutical carrier which can be a sterile liquid or mixture of liquids such as water, saline, aqueous dextrose and related sugar solutions; an alcohol such as ethanol, isopropanol, or hexadecyl alcohol; glycols such as propylene glycol or polyethylene glycol; glycerol ketals such as 2,2-dimethyl-1,3-dioxolane-4-methanol; ethers such as poly(ethyleneglycol) 400; an oil, a fatty acid, a fatty acid ester or glyceride; or an acetylated fatty acid glyceride with or without the addition of a pharmaceutically-acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkylbeta-aminopropionates, and 2-alkyl-imidazoline quarternary ammonium salts, as well as mixtures. The parenteral compositions of this invention will typically contain from about 0.5 to about 25 percent by weight of anti-HIV anionic oligomer in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15 percent by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate.

The achiral anionic oligomers of this invention can also be used prophylactically, that is, to prevent transmission of virus from an infected individual to an uninfected target. Virus is spread via exchange of blood or via exchange of other bodily fluids as well. Thus the oligomers of this invention can be formulated with standard detergent products for use in cleaning, particularly in research and clinical laboratories and in hospitals where blood products of infected individuals are handled. Formulations containing the oligomers of the present invention can be used to clean medical/surgical equipment and utensils as well as the hands of and other skin areas of health care workers. The achiral oligomers of this invention can also be applied, as a liquid or powder composition, to the surface of sexual prophylactic devices, such as condoms, by either the user or manufacturer of the prophylactic device prior to sale. The oligomers of this invention can be formulated into a douche composition for use by females for use prior to subsequent sexual contact with an infected individual. The achiral oligomers of this invention can also be formulated in lubricants and spermacidal jellies and lotions. Finally, the oligomers of this invention can also be formulated as compositions to be added to hot tubs, whirlpool baths and swimming pools to inactivate potential virus activity.

The invention will be further clarified by a consideration of the following examples, which are intended to be purely exemplary of the present invention.

Definitions

The terms used in the present examples are defined as follows, unless stated otherwise, and for example represent an instance of suitable equipment or resins, but similar equipment or differing parameters or resins may be used:

TCID50=tissue culture infectious dose, i.e., the amount of culture fluid effective to infect 50 percent of the cells (50 percent cytopathic effect) at 7 days post infection;

MTT=tetraazolium reduction reagent; 3-(4,5-dimethylthiazol-2-yl)-2,5-diphenyltetrazolium bromide;

RPMI=a cell culture;

RF and GB8 mean HIV-I virus strains;

MT4, $C_{8166}$ and JM=cell lines; and

P24 test-Abbott means an assay of the viral core antigen using the assay kit currently sold by Abbott.

EXAMPLE 1

Preparation of 4,4'-diaminobiphenyl-3,3'-disulfonic Acid of Formula (I)

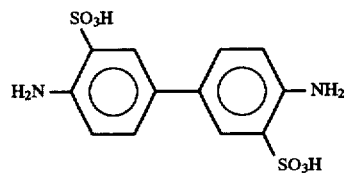

A 500 mL flask equipped with mechanical stirrer, condenser, addition funnel, and thermometer was charged with 50.0 g (0.255 mol) of 2-nitrobenzene sulfonyl chloride (Aldrich). Upon dropwise addition of 5M aqueous sodium hydroxide (125 mL, 0.625 mol) the reaction mixture warmed to 80° C. and a dark red/brown solution resulted. The mixture was stirred for 1 hour and the flask allowed to cool to room temperature. Next, 52.5 g of zinc dust (0.803 mol, Mallinckrodt) was added in one portion. The reaction mixture turned green and warmed to 40° C. Sodium hydroxide (50 percent w/w, 113.75 g, 1.42 mol) was then cautiously added dropwise. The temperature of the reaction mixture rose quickly and vigorous reflux ensued. The reaction mixture turned black, then light green, and finally gray. After addition was complete, the reaction mixture was heated to 90° C. and stirred for 30 minutes. The reaction mixture was cooled and filtered through diatomaceous earth. The zinc salts were washed several times with water yielding 850 mL of an orange/brown filtrate. The filtrate was immediately transferred to a 2 L flask equipped with mechanical stirrer, condenser, addition funnel, nitrogen inlet, and thermometer. Concentrated hydrochloric acid (250 mL) was added dropwise. A light yellow precipitate formed, leaving a clear yellow supernatant (pH=7). Further addition of acid caused the solid to dissolve and the solution to turn orange and then brown (pH=4). More acid caused a tan precipitate to form and persist. After HCl addition was complete, the temperature had risen to 45° C. and the pH was 1. The reaction mixture was stirred for an additional hour and then cooled in an ice bath. The precipitate was collected by filtration and dried in a vacuum oven at ambient temperature yielding a cake which weighed 11.69 g. The product was purified by dissolving it in 150 mL of hot water containing 13.5 mL of 5M sodium hydroxide. Concentrated HCl (15 mL) was then slowly added to reprecipitate the product. Vacuum filtration and drying in a vacuum oven at ambient temperature yielded 11.07 g (28.6 percent) of 4,4'-diaminobiphenyl-3,3'-disulfonic acid.

$^1$H NMR (DMSO-$d_6$): δ 7.86 (1H, d, J=2.26 Hz), 7.58 (1H, d of d), 7.15 (1H, d, J=8.30 Hz);

$^1$H NMR ($D_2O$/NaOD, pH=12): δ 7.87 (1H, m), 7.56 (1H, m), 6.97 (1H, d of d, $J_a$=8.42 Hz, $J_b$=2.62 Hz);

$^{13}$C NMR (DMSO-$d_6$): 137.92, 134.45, 132.19, 127.60, 124.82, 122.09;

$^{13}$C NMR ($D_2O$/NaOD, pH=12): 145.41, 132.70, 131.87, 129.34, 127.05, 121.02;

IR (cm$^{-1}$): 3467, 3071, 2944, 2609, 1524, 1484, 1249, 1196, 1102, 1021, 727, 639; and Elemental Analysis $C_{12}H_{12}N_2O_6S_2$:

|  | C | H | N |
| --- | --- | --- | --- |
| found | 42.08 | 3.20 | 8.09 |
| theory | 41.85 | 3.51 | 8.13 |

EXAMPLE 2

Determination of the achiral nature of diamine of Formula (I)

The achirality of the diamine of Formula (I) and the chirality of the diamine of Formula (II) are illustrated by NMR experiments by two methods, namely, 1) by the chiral salt method and 2) by the chiral end cap method as set forth below in Example 2A, and Example 2B, respectively.

EXAMPLE 2A

Chiral Salt Method

Individual NMR samples were prepared by mixing approximately 15 mg (0.044 mmol) of the desired 4,4'-diaminobiphenyl disulfonic acid with two mole equivalents of the desired amine (benzyl amine, (S)(−)-alpha-phenethylamine) in a 3 mL vial. About ¾ of a mL of dry dimethylsulfoxide-$d_6$ was then added and the vial was placed on a shaker for 30 minutes. The sample was then transferred to a 5 mm NMR tube.

The chirality of 4,4'-diaminobiphenyl-2,2'-disulfonic acid (Formula II) and 4,4'-diaminobiphenyl-3,3'-disulfonic acid (Formula I) was tested by comparing NMR spectra of the desired diamine complexed with either a chiral amine, (S)(−)(α)-phenethyl amine, or an achiral amine, benzyl amine (Eq. 1). ion pairing between chiral ammonium counterions and the sulfonate groups of Formula I or Formula II will produce a pair of diastereomers if the diamine is chiral but not if it is achiral. Evidence for diastereomers and, therefore, chirality of Formula II was found but Formula I was shown to be achiral. In the ¹H NMR spectra (30° C.), each aromatic proton of the diamine (Formula II) showed twice the number of resonances in the presence of (S)(−)(α)-phenethyl amine as it did in the presence of benzyl amine. In the ¹³C NMR spectra (30° C.), some of the resonances for both Formula II and (S)(−)(α)-phenethyl amine were doubled relative to either a pure sample of (S)(−)(α)-phenethyl or Formula II in the presence of benzyl amine.

A 100 mL flask was charged with 0.5 g (1.45 mmol) of 4,4'-diaminobiphenyl-3,3'-disulfonic acid and 30 mL of water. The diamine was dissolved by adding 0.6 mL of 5M NaOH (pH=11). Next, 2.0 g (15 mmol) of (S)(−)(α)-methylbenzyl isocyanate was added and the reaction mixture stirred for 24 hours. Another 2.0 g of the isocyanate was added and the reaction mixture stirred for an additional 24 hours. The reaction mixture was then filtered and the filtrate concentrated by rotary evaporation yielding an off-white solid. The material was dried in a vacuum oven at ambient temperature yielding 450 mg (47 percent) of the non-chiral urea.

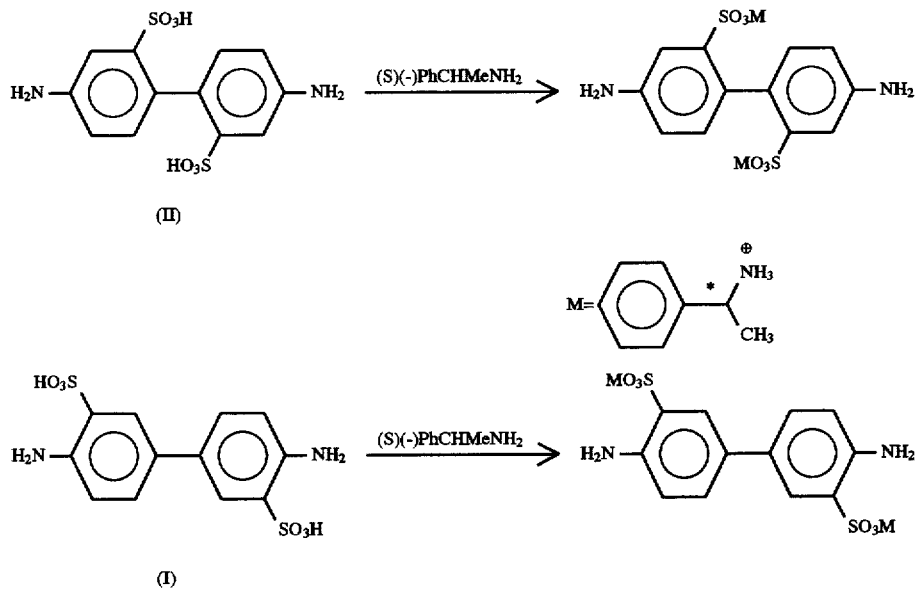

Diamine (Formula I) was shown to be achiral through NMR experiments. Proton and carbon NMR spectra (DMSO-d6) of Formula I in the presence of (S)(−)(α)-phenethyl amine showed no evidence for the presence of diastereomers.

EXAMPLE 2B

Chiral Cap Method

Capping of 4,4'-Diaminobiphenyl-3,3'-disulfonic Acid

¹H NMR (DMBO-d₆): δ 9.54 (1H, s), 9.29 (1H, s), 8.10 (1H, d, J=8.6 Hz), 7.94 (1H, d, J=1.52 Hz), 7.56 (1H, d of d), 7.44 (2H, d, J=8.16 Hz), 7.07 (2H, d, J=8.16 Hz), 2.25 (3H, s);

¹³C NMR (DMSO-d₆):
152.39, 137.56, 135.47, 135.21, 131.74, 130.28, 128.84, 126.46, 123.99, 121.07, 118.68, 20.26.

Capping of 4,4'-Diaminobiphenyl-2,2'-disulfonic Acid Bis (tetra-n-butylammonium) Salt

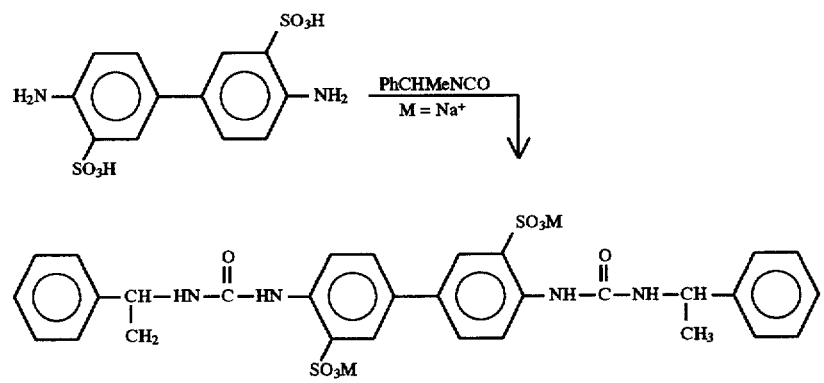

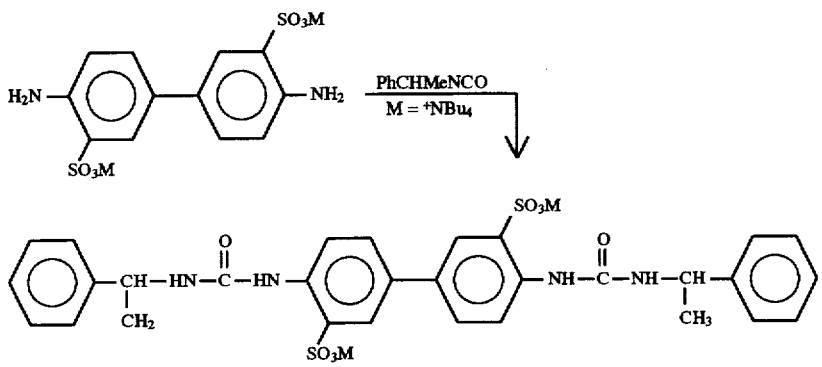

A 100 mL flask was charged with 309 mg (0.374 mmol) of 4,4'-diaminobiphenyl-2,2'-disulfonic acid, bis(tetra-n-butylammonium) salt, 223 mg (1.5 mmol) of (S)(−)(α)-methylbenzyl isocyanate and 10 mL of acetonitrile. After 15 hours, 10 mL of water was added and the reaction mixture stirred for an additional 5 hours. The reaction mixture was filtered and the filter cake dried in a vacuum oven at ambient temperature to yield 61 mg of N,N'-bis-[(S)(α)-methylbenzyl]urea. The filtrate was concentrated by rotary evaporation and the resulting off-white solid was dried in a vacuum oven at 50° C. to yield 300 mg of the urea of the chiral diamine.

$^1$H NMR (DMSO-d$_6$): δ 8.35 (1H, s), 7.66 (1H, m), 7.30 (7H, m), 6.46 (1H, m), 4.84 (1H, m), 3.15 (8H, m), 1.55 (8H, m), 1.30 (11H, m), 0.95 (12H, t);

$^{13}$C NMR (DMSO-d$_6$): 154.41, 145.43, 145.24, 145.12, 137.30, 133.03, 131.36, 128.12, 126.36, 125.65, 57.47, 48.39, 22.98, 19.07, 13.32.

The NMR of the products from the above Examples indicated that the urea from the non-chiral isomer 4,4'-diaminobiphenyl-3,3'-disulfonic acid appears spectroscopically as a single material, whereas 4,4'-diaminobiphenyl-2,2'-disulfonic acid consisted of two compounds, a pair of diastereomers, in approximately equal proportions.

EXAMPLE 3

A General Method of Preparation of the Crude Polydispersed Achiral Polyurea Oligomer A four-neck flask equipped with a dry ice condenser, gas inlet, pH probe, mechanical stirrer, and thermometer was charged with the diamine of Formula I, water, and p-toluidine hydrochloride. A nitrogen stream was passed over the solution and out through a bubbler attached to the dry ice condenser. The bubbler outlet was connected to a gas scrubber through which tap water flowed continuously during the runs. This was used mostly as a precaution in case phosgene managed to pass through the dry ice condenser. A 1 L 316 stainless steel holding cylinder was partially filled with phosgene under pressure. The outlet from this cylinder was connected through a valve to a tee in the nitrogen line used to purge the reaction vessel. The weight of this cylinder was monitored with a balance sensitive to 0.1 g changes. The entire apparatus was assembled in a well ventilated hood. The air inside the hood was monitored for phosgene leaks using phosgene sensitive tape (MDA Scientific, inc.).

The flask was cooled using an ice-water bath. The pH of the reaction mixture was adjusted to and held at a predetermined value by addition of aqueous NaOH. The pH was monitored with a Radiometer pH meter (Type PHM26c) and NaOH was added via a titrator (Radiometer Type TTT11b) and an autoburette (Radiometer ABU12). When the temperature had dropped to 5° C., phosgene was added to the nitrogen stream. The reaction was monitored by HPLC.

RESTRICTING THE CRUDE OLIGOMER MIXTURE TO A NARROWER POLYDISPERSED OLIGOMER MIXTURE

Step 1:
Fractionation Using Gel Filtration Chromatography

A gel filtration column (2.5×95 cm) was slurry-packed with Pharmacia Sephadex™ G-25 resin (crosslinked dextran). A constant flow rate was maintained through the column using a Gilson Minipuls peristaltic pump. A Foxy 200 fraction collector was used to collect fractions at timed intervals. The eluent was monitored at 310 nm (Isco model UA-5 ultraviolet detector) for the presence of polymer. A solution (about 0.5 g in 20 mL water) of the crude sulfonated polyurea was applied to the top of the column. A small band at 35 to 55 minutes, which contained mostly short uncapped oligomers, preceded a much larger band which started at 82 minutes and lasted until 210 minutes. The initial fractions collected during the latter band contained monocapped polyurea, and the higher molecular weight fully-capped polyureas. Later fractions were enriched in low molecular weight fully-capped polyureas.

A few of these fractions were analyzed by HPLC, and the number average and weight average molecular weights of the fractions were calculated according to standard methods (Macromolecules, Hans-Georg Elias, Volume 1, Chapter 8, Plenum Press, 1984). The results are set forth in Table I below.

TABLE I

| Fraction Number | Mn | Mw | Dispersity (Mw/Mn) |
|---|---|---|---|
| 8 | 2340 | 2517 | 1.08 |
| 12 | 2032 | 2262 | 1.11 |
| 16 | 1961 | 2202 | 1.12 |
| 20 | 1212 | 1742 | 1.44 |

ISOLATING THE MONODISPERSED OLIGOMER AS ITS AMMONIUM SALT

Step 2
Analytical and Preparative Liquid Chromatography

The aqueous eluent (50 mM Et$_3$NHOAc) was prepared as follows. Acetic acid (15.0 g, 0.25 mole) was added to 400 mL deionized water. Triethylamine (must be HPLC grade)

was added with stirring until the pH rose to 6.0. Additional water was added to raise the total volume to 0.500 L. This concentrate was sealed and stored at about 3° C. Portions were removed and diluted by a factor of 10 to prepare the LC (liquid chromatography) eluent.

Analytical and preparative liquid chromatography was performed on a Hewlett-Packard model 1090 liquid chromatograph. For analytical work the instrument was equipped with an Alltech Adsorbosphere HS-$C_{18}$ reverse phase column (100 mm×4.6 mm ID, 3 μm particles) using a 0.5 mL/min. of 50 mM aqueous $Et_3NHOAc/CH_3CN$ gradient 30/70 $CH_3CH/Et_3NHOAc$ to 50/50 $CH_3CN/Et_3NHOAc$ at 12 minutes). A diode array detector set to 280 nm (bandwidth 16 nm) referenced to 550 nm (bandwidth 100 nm) was used. A 1 μL aqueous solution of a sample (about 5 mg/mL) was injected.

Preparative LC was performed using a Alltech Adsorbosphere™ HS-$C_{18}$ column filled with 7 μm particles, 10 mm ID by 250 mm long, with the diode array detector set to 340 nm (4 nm bandwidth). The eluent (1.0 mL/min. flow rate) was $Et_3NHOAc/CH_3CN$ (40/60 $CH_3CN/Et_3NHOAc$ changing to 50/50 at 12 minutes). A sample concentration of about 10 percent (w/v) in water was used, with 50 μL injected each time. The column eluent was diverted to a fraction collector (Foxy 200). Four fractions were collected, which consisted of monodispersed oligomers with 1 through 4 repeat units (molecular weights of 813, 1386, 1959, and 2531, respectively). Each fraction was evaporated and dried in a 50° C. vacuum oven overnight, to give an off-white solid. These fractions (triethylammonium salts of the monodisperse urea oligomers of Formula III above) were characterized by analytical LC, proton NMR, and mass spectroscopy (laser desorption time-of-flight).

ION EXCHANGE OF ALKYLAMMONIUM SALTS FOR SODIUM

Step 3

Individual fractions from preparative LC were dissolved in deionized water, and passed through a plastic cartridge column (Alltech Maxi-Clean SCX) packed with sulfonated crosslinked polystyrene beads in the sodium form. Larger amounts of oligomers as the $nBu4N^+$ salts have been converted similarly using a column (2.5 cm ID×10 cm length) filled with MSC-1H (The Dow Chemical Company) beads, which have a capacity of about 1 meq per gram of wet beads (as normally supplied). These columns can be used to exchange ammonium ions for sodium by prewashing them with 2–3 column volumes of NaCl (0.1M) followed by thorough rinsing with deionized water.

EXAMPLE 4

Preparation of Capped Polyurea Oligomers

A 500 mL flask was charged with 2.00 g (5.81 mmol) of 4,4'-diaminobiphenyl-3,3'-disulfonic acid, 0.27 g (1.88 mmol) of p-toluidine hydrochloride (Kodak) and 250 mL of water. The initial pH of the slurry was 2.4. The pH was brought to 6.0 by addition of 5M NaOH yielding a clear brown solution. Phosgene (8.4 g, 85 mmol) was added over 10 minutes and the pH was held constant at 6 by addition of 5M NaOH. A purple/blue solid fell from solution as the polymerization proceeded (we have observed that the polymer is less soluble at high salt concentrations). HPLC analysis of the reaction mixture revealed that little of the polyurea was fully capped. The reaction mixture was then concentrated to 50 mL by rotary evaporation and filtered.

The filter cake was dissolved in 200 mL of water and reacted with p-tolyl isocyanate. A total of 3.0 g (22.5 mmol) of the isocyanate was added in 0.5 g aliquots over the course of 7 days. The reaction mixture was then filtered to remove N,N'-bis(4-methylphenyl)urea. The filtrate was concentrated by rotary evaporation at 40 mL and then subjected to gel filtration chromatography. The number average molecular weight of this polydispersed polyurea was estimated to be 1,960 (n=4 in Formula III) by HPLC.

EXAMPLE 5

Preparation of Capped Polyurea Oligomers

A 500 mL flask was charged with 1.0 g (2.9 mmol) of 4,4'-diaminobiphenyl-3,3'-disulfonic acid and 200 mL of water. The pH of the reaction mixture was increased to 7.0 by addition of 0.99 mL of 5M NaOH yielding an orange/brown solution. p-Tolyl isocyanate (1 g, 7.5 mmol) was added and the reaction mixture stirred for 3 hours. The progress of the capping reaction was monitored by HPLC. Phosgene (15 g, 152 mmol) was added over 45 minutes and the pH was held at 7.0 by addition of 5M NaOH. The reaction mixture was filtered and the filtrate concentrated to 75 mL by rotary evaporation to salt out the desired oligomers. The slurry was filtered yielding a gray solid. The solid was taken up in 10 mL of water and filtered through a 1 micron PTFE syringe filter. One fourth of this sample was subjected to preparative HPLC. Preparative HPLC samples were individually concentrated by rotary evaporation and then placed in a vacuum oven at ambient temperature overnight to remove $Et_3NHOAc$ as triethyl amine and acetic acid. The samples were then redissolved in water and passed through a syringe mounted ion exchange cartridge to convert the counter ion associated with the sulfonate groups from triethylammonium to sodium. The solutions were evaporated using a stream of nitrogen and then dried in a vacuum oven at ambient temperature yielding:

n=1, 22.0 mg $^1$H NMR ($D_2O$): δ 8.00 (2H, bs), 7.81 (1H, d, J=8.55 Hz), 7.80 (1H, d, J=8.74 Hz), 7.50 (2H, m), 7.15 (2H, s, J=8.54 Hz), 7.08 (2H, d, J=8.54 Hz), 2.17 (3H, s);

$^{13}$C NMR ($D_2O$): 156.65, 155.26, 137.36, 136.67, 136.40, 136.25, 136.01, 135.57, 134.63, 134.60, 134.39, 131.97, 127.15, 127.03, 125.21, 123.27, 22.31.

n=2, 23.5 mg $^1$H NMR ($D_2O$): δ 7.99 (3H, bs), 7.84 (3H, m), 7.41 (3H, m), 7.16 (2H, d, 8.33 Hz), 7.07 (2H, d, 8.33 Hz), 2.16 (3H, s);

$^{13}$C NMR ($D_2O$): 156.78, 155.43, 137.37, 136.70, 136.49, 136.33, 136.08, 135.68, 134.84, 134.64, 131.98, 127.21, 127.08, 125.34, 123.40, 22.28.

EXAMPLE 6

Preparation of Noncapped Polyurea Oligomers

A 500 mL flask was charged with 2.0 g (5.81 mmol) of 4,4'-diaminobiphenyl-3,3'-disulfonic acid and 250 mL of water. Aqueous sodium hydroxide (5M, 2.35 mL) was added to dissolve the diamine and bring the pH up to 6.0. Phosgene (11.2 g, 0.266 mol) was added over the course of 20 minutes and the pH held at 6.0 by addition of aqueous NaOH. As the reaction proceeded, a blue/gray precipitate formed. After all of the phosgene had been consumed, the reaction mixture was filtered to yield a purple/blue solid. The solid was dried in a vacuum oven at ambient temperature, yielding 2.3 g of product. The number average molecular weight of the polydispersed material was determined to be 8.5 by proton NMR.

BIOLOGICAL DATA

Example I

ABILITY OF AN ANTI-HIV OLIGOMER TO PREVENT SYNCYTIA FORMATION AND EXPRESSION OF P24 VIRAL CORE ANTIGEN USING JM CELLS AND GB8 VIRUS STRAIN

To show that an oligomer of the invention blocks HIV infection, CD4$^+$ T-cells (JM) were exposed to the GB8 strain of HIV-I, GB8. The virus was first incubated with an oligomer for 15 minutes and then the cells were added. After 2 hours adsorption, the virus innoculum was removed, the cells were washed three times to remove traces of input virus and the cells were incubated in the presence of the compound. Antiviral activity was determined after 3 days incubation by plotting the mean number of syncytia found in quadruple cultures against $\log_{10}$ concentration of anionic polymer or of other test compounds. The potency of an oligomer was also measured by assaying viral core antigen (P24 test-Abbott) in the supernatant fluid. Heparin, dextran sulfate, vs CD4, ATZ and/or ddC data, when included in any of the following Tables, are provided as positive controls.

The data are summarized in Table II.

TABLE II

| Compound  | ED$_{50}$+ (μg/ml) |
|-----------|---------------------|
| Example 4 | 0.48                |
| Example 6 | 0.19                |

+Effective dose yielding 50 percent inhibition of HIV-1 induced syncytia formation of JM cells by the GB8 viral strain ABILITY OF AN ANTI-HIV OLIGOMER TO PREVENT HIV-INDUCED CELL DEATH USING MT-4 CELLS AND THE RF VIRUS STRAIN In this experiment, 1.5 mL of RPMI medial was added to each tube to dissolve the test compound. Compounds were then assayed for HIV-I activity by making doubling dilutions of the solutions across a microtitre plate. $5 \times 10^4$ cells and 100 TCID$_{50}$ units of virus were then added to each well and the plates incubated at 37° C. for 7 days. MTT was added to each well and the plates incubated for a further two hours. The blue formazan crystals were dissolved using acid isopropanol and the absorbance measured at 540 nm.

The data are illustrated in Table III below.

TABLE III

| Compound  | ED$_{50}$+ (μg/ml) | CD$_{50}$* (μg/ml) |
|-----------|---------------------|---------------------|
| Example 4 | 4.4                 | ≧100                |
| Example 6 | 2.7                 | ≧100                |

+Effective dose yielding 50 percent inhibition of HIV-1 induced cell death of MT-4 cells by the RF viral strain in the MTT assay.
*Cytoxic dose of compound yielding 50 percent toxicity to MT-4 cells in the MTT assay.

EFFECT OF ANTI-HIV OLIGOMERS ON THE GROWTH OF HIV-IRF IN THE C8166 T CELL LINE

Protocol: C8166 cells were infected with HIV-I$_{RF}$ for one hour at room temperature. The cells were then washed twice in RPMI and distributed into wells of a tissue culture plate containing varying concentrations of test compound or no compound (control). After 3 days incubation at 37° C., the cells were observed for the presence of syncytia and the cell-free supernatant fluid was assayed for levels of P24 viral core antigen using an ELISA. The results are set forth in the Tables IV and V below.

TABLE IV

| COMPOUND  | CONC. μg/mL | SYNCYTIA | P24 (pg/mL) | % CONTROL |
|-----------|-------------|----------|-------------|-----------|
| Example 4 | 100         | 0        | Negative    | 0         |
|           | 0           | +        | 107550      | 26        |
|           | 1           | ++       | 460270      | >100      |
|           | 0.1         | +++      | 641860      | >100      |
|           | 0.01        | +++      | 648390      | >100      |
| Example 6 | 100         | 0        | Negative    | 0         |
|           | 10          | 0        | Negative    | 0         |
|           | 1           | +        | 159810      | 39        |
|           | 0.1         | +/++     | 303510      | 75        |
|           | 0.01        | +++      | 293710      | 72        |

TABLE V

| Compound  | ED$_{50}$(μg/ml)+ |
|-----------|---------------------|
| Example 4 | 4.8                 |
| Example 6 | 0.5                 |

+Effective dose yielding 50 percent inhibition of HIV-1 induced syncytia and P24 viral antigen scores in C98166 cells infected with the RF viral strain.

What is claimed is:

1. A water-soluble, rigid backbone, achiral, polyurea oligomer having a number average molecular weight of <20,000 and of the Formula:

$$R^1 \!-\!\!\left[\!\begin{array}{c}H\\N\end{array}\!-\!\!\begin{array}{c}O\\\|\\C\end{array}\!\right]_m\!\!-\!\!\left[\!\begin{array}{c}H\\N\end{array}\!-\!\!\!\underset{SO_3R}{\overset{RO_3S}{\bigcirc\!\!-\!\!\bigcirc}}\!\!\!-\!\!\begin{array}{c}O\\\|\\N\!-\!C\end{array}\!-\!\!\begin{array}{c}H\\N\!-\!R^2\end{array}\!\right]_n$$

wherein:

R is hydrogen or a pharmaceutically acceptable cation;

R$^1$ is hydrogen, C$_1$–C$_4$ alkyl, phenyl, or a phenyl with 1 or 2 SO$_3$R substituents and up to 3 additional substituents independently selected from a group consisting of a chloro, bromo and C$_1$–C$_4$ alkyl radical;

R$^2$ is —R$^1$ or —X—NHR$^1$, wherein R$^1$ is as defined above;

X is a divalent radical of the formula:

m is 0 or 1, with the proviso that when m is 0, $$\underset{SO_3R}{\overset{RO_3S}{\bigcirc\!\!-\!\!\bigcirc}}$$

R$^1$ is hydrogen; and n is an integer from 3 to 50.

2. The oligomer of claim 1, wherein R is hydrogen, m is 1, R$^1$ and R$^2$ are 4-methylphenyl.

3. An oligomer of claim 2, wherein R is a pharmaceutically acceptable cation.

4. The oligomer of claim 1, m is 0, R and $R^1$ are hydrogen $R^1$ and $R^2$ is:

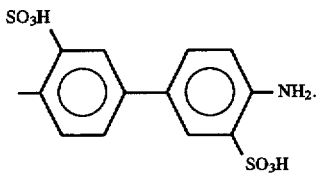

5. The oligomer of claim 1 wherein the oligomer is narrow polydispersed having a polydispersity ratio from 1.0 to 1.3.

6. The oligomer of claim 1 wherein the oligomer is narrow polydispersed having a polydispersity ratio from 1.0 to 1.2.

7. The oligomer of claim 1 wherein the oligomer is monodispersed having a polydispersity ratio from 1.0 to 1.1.

8. The oligomer of claim 2 wherein the oligomer is narrow polydispersed having a polydispersity ratio from 1.0 to 1.3.

9. The oligomer of claim 2 wherein the oligomer is narrow polydispersed having a polydispersity ratio from 1.0 to 1.2.

10. The oligomer of claim 2 wherein the oligomer is monodispersed having a polydispersity ratio from 1.0 to 1.1.

11. The oligomer of claim 4 wherein the oligomer is narrow polydispersed having a polydispersity ratio from 1.0 to 1.3.

12. The oligomer of claim 4 wherein the oligomer is narrow polydispersed having a polydispersity ratio from 1.0 to 1.2.

13. The oligomer of claim 4 wherein the oligomer is monodispersed having a polydispersity ratio from 1.0 to 1.1.

14. The oligomer of claim 1 which is narrow monodispersed, have a polydispersity ratio of from 1.0 to 1.1.

15. A pharmaceutical composition having anti-HIV activity, comprising a pharmaceutically-acceptable carrier and a compound which is a water-soluble, rigid backbone, achiral, polyurea oligomer having a number average molecular weight of <20,000 of the Formula:

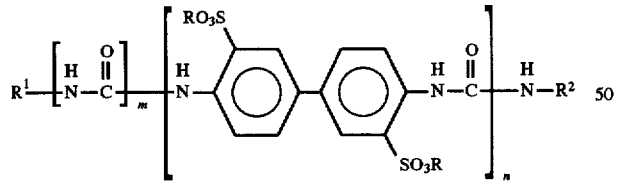

and further comprising pharmaceutically acceptable salts, wherein:

R is hydrogen or a pharmaceutically acceptable cation;

$R^1$ is hydrogen, $C_1$–$C_4$ alkyl, phenyl, or a phenyl with 1 or 2 $SO_3R$ substituents and up to 3 additional substituents independently selected from a group consisting of a chloro, bromo and a $C_1$–$C_4$ alkyl radical;

$R^2$ is —$R^1$ or —X—$NHR^1$, wherein $R^1$ is as defined above;

X is a divalent radical of the formula:

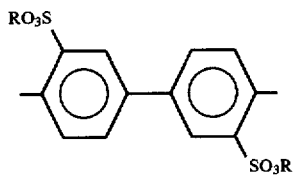

m is 0 or 1, with the proviso that when m is 0, $R^1$ is hydrogen; and n is an integer from 3 to 50.

16. A pharmaceutical composition of claim 15 further comprising a detergent.

17. The pharmaceutical composition of claim 15 which is in the form of a liquid, powder, douche, jelly or lotion.

18. A method of treating a patient afflicted with AIDS or ARC which comprises administering to a patient in need thereof an effective amount of a compound and the pharmaceutically acceptable salts of a water-soluble, rigid backbone, achiral, polyurea oligomer having a number average molecular weight of <20,000 and of the Formula:

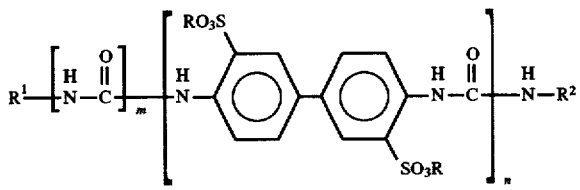

wherein:

R is hydrogen or a pharmaceutically acceptable cation;

$R^1$ is hydrogen, $C_1$–$C_4$ alkyl, phenyl, or a phenyl with 1 or 2 $SO_3R$ substituents and up to 3 additional substituents independently selected from a group consisting of a chloro, bromo and $C_1$–$C_4$ alkyl radical;

$R^2$ is —$R^1$ or —X—$NHR^1$, wherein $R^1$ is as defined above;

X is a divalent radical of the formula:

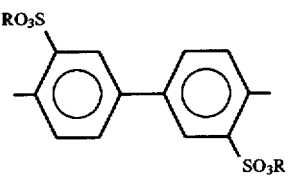

m is 0 or 1, with the proviso that when m is 0, $R^1$ is hydrogen; and n is an integer from 3 to 50.

19. The method of claim 18 wherein the viral infection is AIDS or ARC.

20. The method or claim 19 wherein the administration is done orally or parenterally.

21. A method of preventing an HIV infection in a patient in need thereof which comprises administering to a patent in need thereof an effective amount of a compound and the pharmaceutically acceptable salts of a water-soluble, rigid backbone, achiral, polyurea oligomer having a number average molecular weight of <20,000 and of the Formula:

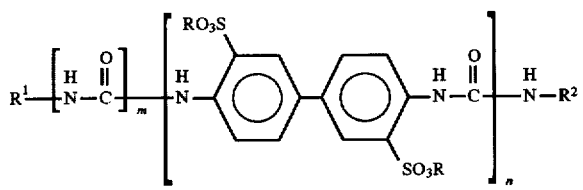

wherein:

R is hydrogen or a pharmaceutically acceptable cation;

$R^1$ is hydrogen, $C_1$-$C_4$ alkyl, phenyl, or a phenyl with 1 or 2 $SO_3R$ substituents and up to 3 additional substituents independently selected from a group consisting of a chloro, bromo and $C_1$-$C_4$ alkyl radical;

$R^2$ is —$R^1$ or —X—$NHR^1$, wherein $R^1$ is as defined above;

X is a divalent radical of the formula:

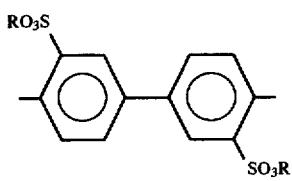

m is 0 or 1, with the proviso that when m is 0, $R^1$ is hydrogen; and n is an integer from 3 to 50.

22. The method of claim 21 wherein the administration is done topically.

23. A process for preparing a narrow-poly- and monodispersed, water-soluble, rigid backbone, achiral polyurea oligomer of the formula:

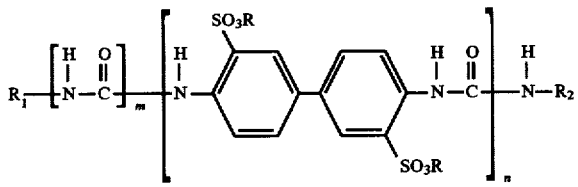

wherein:

R is hydrogen or a pharmaceutically acceptable cation;

$R^1$ is hydrogen, $C_{1-4}$ alkyl, phenyl, or a phenyl with 1 or 2 $SO_3R$ substituents and up to 3 additional substituents independently selected from the group consisting of a chloro, bromo and $C_{1-4}$ alkyl radical;

$R^2$ is —$R^1$ or —X—$NHR^1$, wherein $R^1$ is as defined above;

X is a divalent radical of the formula:

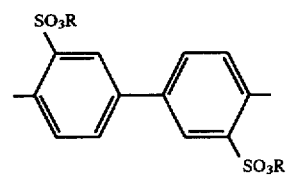

m is 0 or 1, with the proviso that when m is 0, $R^1$ is hydrogen; and n is an integer from 3 to 50;

which comprises restricting the corresponding crude polydispersed anionic oligomer mixture to a narrow polydispersed anionic oligomer mixture having a polydispersity ratio from 1.0 to 1.3 by means of gel filtration, selective precipitation, membrane permeation or reverse phase chromatography.

24. The process of claim 23 further comprising the step of convening the narrow poly-dispersed anionic oligomer mixture to a pharmaceutically-acceptable salt.

25. The process of claim 23 further comprising the step of isolating the monodispersed oligomer.

26. The process of claim 25 further comprising the step of converting the monodispersed oligomer into a pharmaceutically-acceptable salt.

27. The process of claim 25 wherein n is a monodispersed fraction from 3 to 15.

28. The process of claim 25 wherein n is a monodispersed fraction from 5 to 10.

29. The process of claim 25 wherein n is a monodispersed fraction from 6 to 9.

30. The process of claim 24 wherein the salt is an ammonium salt.

31. The process of claim 26 wherein the salt is a ammonium salt.

32. The process of claim 24 wherein the salt is a sodium salt.

33. The process of claim 26 wherein the salt is a sodium salt.

34. The process of claim 24 wherein the salt is a potassium salt.

35. The process of claim 26 wherein the salt is a potassium salt.

36. The process of claim 24 wherein the restriction is carried out by employing one or more of the techniques of gel filtration, selective precipitation, membrane permeation and reverse phase chromatography.

37. The process of claim 25 wherein the restriction is carried out by employing one or more of the techniques of gel filtration, selective precipitation, membrane permeation and reverse phase chromatography.

38. The process of claim 26 wherein the restriction is carried out by employing one or more of the techniques of gel filtration, selective precipitation, membrane permeation and reverse phase chromatography.

39. The process of claim 23 wherein the restriction is carried out by employing gel filtration.

40. The process of claim 24 wherein the restriction is carried out by employing gel filtration.

41. The process of claim 25 wherein the restriction is carried out by employing gel filtration.

42. The process of claim 26 wherein the restriction is carried out by employing gel filtration.

43. The process of claim 25 wherein the isolation is carried out by employing gel electrophoresis or reverse phase chromatography.

44. The process of claim 26 wherein the isolation is carried out by employing gel electrophoresis or reverse phase chromatography.

45. The process of claim 24 wherein the further step of converting the narrow poly-dispersed anionic oligomer mixture to a pharmaceutically-acceptable salt is carried out by employing ion-exchange.

46. The process of claim 26 wherein the further step of converting the narrow poly-dispersed anionic oligomer mixture to a pharmaceutically-acceptable salt is carried out by employing ion-exchange.

47. The process of claim 27 wherein the purity of the monodispersed material is at least 75 percent.

48. The process of claim 27 wherein the purity of the monodispersed material is from about 85 to about 100 percent.

49. The process of claim 23 wherein the oligomer polydispersity ratio is from 1.0 to 1.2.

50. The process of claim 23 wherein the oligomer polydispersity ratio is from 1.0 to 1.15.

* * * * *